United States Patent [19]

Fenner

[11] Patent Number: 5,214,387

[45] Date of Patent: May 25, 1993

[54] ELECTROLYTIC RESISTIVITY LEAK DETECTOR

[76] Inventor: Richard D. Fenner, 7303 Springside, Houston, Tex. 77040

[21] Appl. No.: 319,615

[22] Filed: Mar. 6, 1989

[51] Int. Cl.⁵ .................. G01R 27/22; G01N 17/00
[52] U.S. Cl. .................. 324/557; 324/700; 324/718; 73/86; 340/605
[58] Field of Search .......... 324/71.2, 700, 557, 324/693, 715, 718, 722, 724; 340/603, 604, 605; 73/86; 204/153.11, 404; 436/3, 5, 6, 178; 422/53, 82.02

[56] References Cited

U.S. PATENT DOCUMENTS

| | | | |
|---|---|---|---|
| 3,197,724 | 7/1965 | Marsh | 324/71.2 X |
| 3,782,181 | 1/1974 | Gutler | 73/86 |
| 3,996,124 | 12/1976 | Eaton et al. | 73/86 X |
| 4,158,806 | 6/1979 | Kotylev et al. | 324/700 |
| 4,365,788 | 12/1982 | Block | 73/86 X |
| 4,655,077 | 4/1987 | Purvis et al. | 73/86 |

Primary Examiner—Jack B. Harvey
Attorney, Agent, or Firm—Alton W. Payne

[57] ABSTRACT

The electrolytic resistivity leak detector comprises the method of electrical resistivity to measure the gradual intrusion of aggressive chemicals into the wall of a plastic or fiber reinforced plastic vessel. This device and method includes the use of electric sensors within the wall of the vessel. The sensors provide an electrical circuit as the chemicals permeate through the wall and make contact with the sensors. A microammeter is included as an instrument to monitor and register the degree of electrical resistivity caused by the chemical intrusion.

7 Claims, 1 Drawing Sheet

ELECTROLYTIC RESISTIVITY LEAK DETECTOR

FIELD OF THE INVENTION

The invention relates generally to a device to monitor the changes in the electrical resistivity in a plastic or a fiber reinforced plastic structure caused by the gradual permeation of aggressive chemicals through the wall of the structure.

DESCRIPTION OF THE RELATED ART

The Environmental Protection Agency has issued guidelines (264.191-264.193) for the containment and detection of leaks of aboveground and belowground storage tanks and pipes that contain hazardous materials that could discharge into ground water, subsurface water, or subsurface soils (280.1). Many of the storage tanks containing hazardous materials are nonmetallic vessels made of plastic or fiber reinforced plastic materials. The existing detection processes detect liquids after they have leaked into the soils, or make volumetric measurements of liquids in storage tanks. There is nothing available that can measure the rate of permeation through the wall of nonmetallic vessels. There is a need in industry for such a device so supervisory personnel can have opportunity to monitor the gradual chemical intrusion into the wall. Such monitoring will reveal the need to act to prevent a weakening of the structure and a potential failure. Appropriate action could then be taken before repair costs become prohibitive and before the environment or worker safety is affected.

SUMMARY OF THE INVENTION

The present invention provides a method and device for monitoring the chemical integrity of nonmetallic vessels such as plastic and fiber reinforced plastic vessels. By measuring electrical resistivity of a vessel wall, the gradual intrusion of aggressive chemicals through the wall can be tracked. The device includes a preembedded wet common reference point and at least one dry reference point. These reference points are connected to form an electrical circuit. As an aggressive chemical permeates the wall, the wall resistivity changes and the change is registered on a meter.

In one feature of the invention, a monitoring system tracks aggressive chemicals as they penetrate the wall so that proper action can be taken before the structure is weakened or the environment or worker safety is affected.

DETAILED DESCRIPTION OF THE PREFERRED EMBODIMENT

Figure 1:
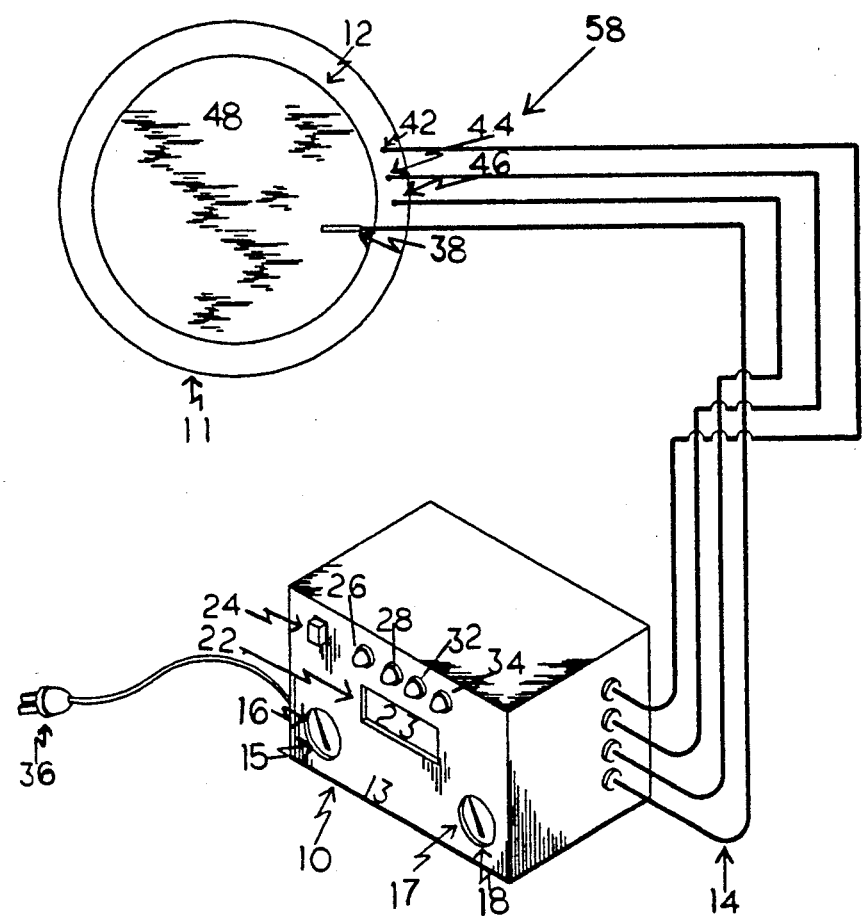
FIG. 1 illustrates the monitoring system of the present invention, including a monitor and wet and dry reference points within the structure being monitored.

FIG. 1 illustrates the monitoring system of the present invention. The monitoring system includes a monitor 10 connected to a structure 11 at a structural wall 12 through a connecting electrical cord 14 that is able to handle 12-15 volts DC current. The connecting cord 14 is a four conductor wire. The cord 14 attaches to a wet common reference point 38 that extends through the wall 12 into an inside environment 48 of the structure 11. The common reference point 38 is a first reference point. The cord 14 also connects to three dry reference points 42, 44, and 46 that are embedded at various depths within the wall 12. Any of the points 42, 44, and 46 is a second reference point. The cord 14 connects the three dry reference points 42, 44, and 46 to a depth reference point dial 16 on the monitor 10. The depth reference point dial 16 allows the operator to select and monitor a specific reference point 42, 44, or 46.

A front face 13 of the monitor 10 has the depth reference point dial 16, a run/test/alarm-off dial 18, a digital microammeter 22, an on-off switch 24, and four colored lights 26, 28, 32, and 34. The microammeter 22 is a current measurer. The light 26 is amber and indicates that current is on. The light 28 is green and indicates safe operating conditions. The light 32 is blue and indicates initial mild current flow. The light 34 is red and indicates chemical penetration at the dry reference point selected by the dial 16. A 115 volt power cord 36 provides power for the monitor 10. The run/test/alarm-off dial 18 has three settings, a "Run" setting 52 for operational use, a "Test Meter" setting 54 for checking to see if the digital microammeter 22 is operational, and an "Alarm Off" setting 56 to disengage an alarm buzzer 96.

Figure 2:
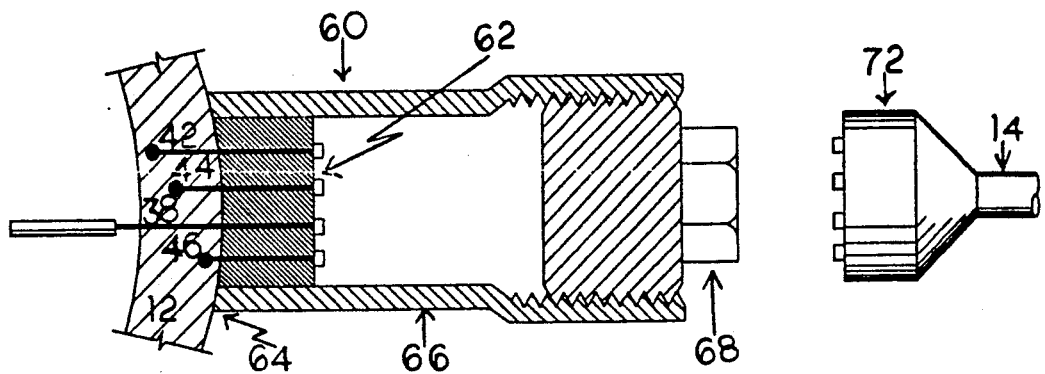
FIG. 2 is a sectional view of the side of the wall of the structure of FIG. 1, depicting the reference points and an outlet for connecting wires to the monitor.

FIG. 2 is a labeled sectional view of the side of the structural wall 12. This figure shows the inside environment 48 of the structure 11 with the wet common reference point 38 extending through the wall 12 and the three dry reference points 42, 44, and 46 at different depths embedded within the wall 12. These reference points 38, 42, 44, and 46 are attached to a connector station 60 which houses a 4-inlet female electrical receptical 62 (Part #S204SB, TRW Electronic Components Group, El Segundo, Calif.). The connector station 60 is attached to the wall 12 with a gusseted joint 64. The connector station 60 is made up of a plastic weather proof cylinder 66 that contains a weather proof cap 68. Connection to the monitor 10 includes the electrical cord 14 that has a 4-prong male plug 72 (Part #P2404CCT, TRW Electronics Components Group, El Segundo, Calif.).

An operator turns a rotary switch 17. The switch 17 is a 4-pole, 3-position switch, type A40315RN2Q, made by C & K Components, Inc., Newton, Mass. The position of the switch 17 is indicated by the run/test/alarm-off dial 18. In the "Run" position the switch 17 completes the electrical circuit to the reference points 58. The dry reference points 42, 44, and 46 are made of steel, copper, or aluminum. The wet reference point 38 that extends into the environment 48 is made of a highly corrosion resistant alloy that handles the particular needs of the inside environment 48. Metals and alloys that are used for the reference point 38 include any of the following: 304 and 316 stainless steels, MONEL (as defined in the standard literature associated with the art, e.g., "Metals & Alloys in the Unified Numbering System," Fifth Edition, June 1989, Society of Automotive Engineers, Inc./American Society for Testing and Materials), nickel, HASTELLOY B/C, (as defined in the standard literature associated with the art, e.g., "Metals & Alloys in the Unified Numbering System," Fifth Edition, June 1989, Society of Automotive Engineers, Inc./American Society for Testing and Materials), titanium, zirconium, tantalum, and platinum. The reference points 58 connect to the monitor 10 by an electrical four conductor cable 14 (model #T9444 made by Belton Corporation, Monticello, Ky.).

The operator then turns a rotary switch 15. The switch 15 is a 4-pole, 3-position, type #A40315RN2Q, made by C & K Components, Newton, Mass. The position of the switch 15 is indicated by the depth reference point dial 16. The switch 15 completes the circuit between the embedded dry reference point 42, 44, or 46, and the wet common reference point 38. The amount of the electrical current in the circuit depends on the depth and amount of penetration into the wall 12 by the aggressive chemicals.

As the amount of intrusion of aggressive chemicals gradually makes contact with the dry reference points 42, 44, 46, it gives a current input 76 to the digital microammeter 22 (model #4500, ISL Corporation, Worcester, Mass.). The digital microammeter 22 responds by increasing the digital readout 23.

Although the present invention is illustrated in the drawings and previously described in detail, this invention contemplates any configuration and design of components which will accomplish the equivalent result. As an example, the embodiment of the invention can use a macroammeter or use a megohmmeter. It could also use a computer instead of the microammeter to generate the readout 23. An another example, the invention could use any number of dry reference points. The wet common reference point could be embedded within the wall instead of protruding into the interior of the structure. Thus the wet reference point would only become wet when permeation reaches it. As another example, the dry reference point does not need to be a point at all but could be a conductive cloth or mat such as carbon or graphite. The mat could be built into the entire structural wall at the same distance from the interior surface of the wall. As a final example the connector station does not have to fit directly on the wall but can be mounted elsewhere. The connector station can connect to the reference points by way of a longer cable. Such connection would be required in difficult to reach areas.

It is applicant's invention in the following claims to cover modifications and variations as fall within the true spirit and scope of the invention.

What is claimed is:

1. Apparatus for measuring electrical resistivity and the changes therein, of the interior wall of any nonmetallic reinforced plastic vessel caused by the gradual permeation of electrolytic chemicals from the interior surface of the structure to the exterior surface of the structure, the apparatus comprising:
    (a) a first sensor on the interior surface of the vessel and exposed to the electrolytic chemicals,
    (b) a second sensor in the vessel wall located closer to the interior surface than the exterior surface of the vessel and remote from initial exposure to the electrolytic chemicals,
    (c) a third sensor in the vessel wall located approximately equidistant from the interior surface and exterior surface of the vessel, and remote from initial exposure to the electrolytic chemicals,
    (d) a fourth sensor in the vessel located closer to the exterior surface than the interior surface of the vessel and remote from initial exposure to electrolytic chemicals,
    (e) a power source,
    (f) a first conduit for communicating a current from said power source to said first sensor,
    (g) means for measuring the current in operative association with said power source,
    (h) a second conduit for communicating a current from said second, third and fourth sensors to said means for measuring the current,
    (i) means for indicating responses to said second, third and fourth sensors indicative of the status of the engagement of the power source, such that said power source generates an electric current such that the chemical contained inside the vessel is an electrolyte and electric current passed to the electrolyte by said first sensor is measurable wherever the chemical is found; the second, third and fourth sensors are embedded in the wall of the vessel at varying depths for engaging the chemical as it permeates the interior wall of the vessel moving toward the exterior wall, the sensors make electrical contact and an electrical loop is formed, and said means for measuring current measures the electric current detected by the second, third and fourth sensors, such that the second sensor makes initial electrical contact with the electrolytic chemical, followed by the third sensor and subsequently the fourth sensor makes electrical contact with the chemical.

2. The apparatus defined in claim 1, wherein said second, third and fourth sensors are constructed of corrosion resistant metal or alloy.

3. The apparatus defined in claim 1, wherein said second, third and fourth sensors are constructed of copper.

4. The apparatus defined in claim 1, wherein said second, third and fourth sensors are constructed of aluminum.

5. The apparatus defined in claim 1, wherein said first reference sensor is constructed from a corrosion resistant metal or alloy.

6. A process for measuring electrical resistivity of aggressive, electrolytic chemical permeation in and through a plastic fiber reinforced plastic, porous, walled vessel having a first sensor which emits an electric current and is mounted on the interior side of the vessel wall and is exposed to the electrolytic chemical and a second, third and fourth electrical reference sensor, embedded within the wall of the vessel, said process comprising the steps of:
    (a) measuring the electric current of said second, third and fourth reference sensors in comparison to the electrical current emitted by the first reference sensor;
    (b) providing said electrical reference sensors, having highly conductive electrical properties and positioned within the interior wall of the vessel;
    (c) positioning said electrical reference sensors at various positions within the wall of the vessel; and
    (d) allowing for electrical resistivity measurements from the second, third and fourth reference sensors, embedded in the wall of the plastic or fiber reinforced plastic material.

7. A method as defined in claim 6, further comprising positioning the second, third and fourth sensor from an interior wall of the plastic or fiber reinforce plastic vessel.

* * * * *